United States Patent [19]

Giese

[11] Patent Number: 5,178,146
[45] Date of Patent: Jan. 12, 1993

[54] GRID AND PATIENT ALIGNMENT SYSTEM FOR USE WITH MRI AND OTHER IMAGING MODALITIES

[76] Inventor: William L. Giese, 272 Culver, #3, Rochester, N.Y. 14607

[21] Appl. No.: 784,660

[22] Filed: Oct. 25, 1991

Related U.S. Application Data

[63] Continuation of Ser. No. 652,559, Feb. 7, 1991, abandoned, which is a continuation of Ser. No. 266,544, Nov. 3, 1988, abandoned.

[51] Int. Cl.$^5$ .............................................. A61B 5/055
[52] U.S. Cl. ........................... 128/653.2; 128/653.5; 324/308; 324/309
[58] Field of Search ............... 128/653.2, 653.5, 653.1, 128/659; 324/300, 308, 318, 309; 5/601; 378/63

[56] References Cited

U.S. PATENT DOCUMENTS

| | | | |
|---|---|---|---|
| 4,528,510 | 7/1985 | Loeffler et al. | 324/308 |
| 4,551,678 | 11/1985 | Morgan et al. | 324/300 |
| 4,583,538 | 4/1986 | Onik et al. | |
| 4,618,826 | 10/1986 | Smith et al. | |
| 4,629,989 | 12/1986 | Riehl et al. | 324/300 |
| 4,644,276 | 2/1987 | Sierocuk et al. | 324/300 |
| 4,671,256 | 6/1987 | Lemelson | 128/659 |
| 4,692,704 | 9/1987 | Gray. | |
| 4,791,369 | 12/1988 | Yamamoto et al. | 324/308 |
| 4,816,762 | 3/1989 | Bohning | 324/300 |
| 4,826,487 | 5/1989 | Winter | 606/130 |

FOREIGN PATENT DOCUMENTS 0133722 4/1985 European Pat. Off.
0228692 11/1987 European Pat. Off.

OTHER PUBLICATIONS

Zhu et al, "Accuracy of Area Measurements Made from MR Images Compared with Computed Tomography", Journal of Computer Assisted Tomography, vol. 10 No. 1 pp. 96–102 1986.

S. Goerss et al., A Computerized Tomographic Stereotactic Adaptation System, 10 Neurosurgery 375–379 (1982).

P. C. Hajek et al., Localization Grid for MR-guided Biopsy, 163(3) Radiology 825–826 (1987).

S. Miura et al., Anatomical Adjustments in Brain Positron Emission Tomography Using CT Images, 12(2) Journal of Computer Assisted Tomography 363–367 (1988).

M. M. Covell et al., Automated Analysis of Multiple Performance Characteristics in Magnetic Resonance Imaging Systems, 13(6) Medical Physics 815–823 (1986).

*Primary Examiner*—Ruth S. Smith
*Attorney, Agent, or Firm*—Stroud, Stroud, Willink, Thompson & Howard

[57] ABSTRACT

A grid system for interfacing MRI with other imaging modalities. The system includes a grid of contrast material which is compatible with MRI and other imaging modalities and a means to reproducibly position the subject in relation to the grid. The grid system is also used to plan radiotherapy and surgical biopsy procedures.

4 Claims, 4 Drawing Sheets

UNCORRECTED IMAGE

COMPUTER ALGORITHM

CORRECTED IMAGE

GRID AND PATIENT ALIGNMENT SYSTEM FOR USE WITH MRI AND OTHER IMAGING MODALITIES

This is a continuation of application Ser. No. 07/652,559, filed Feb. 7, 1991, now abandoned, which is a continuation of application Ser. No. 07/266,544, filed Nov. 3, 1988, now abandoned.

TECHNICAL AREA

The invention relates to the area of diagnostic imaging and more specifically to a method and device for interfacing MRI with various other diagnostic imaging modalities and treatment devices.

BACKGROUND OF THE INVENTION

Magnetic resonance imaging (MRI) is a recent but extremely powerful noninvasive diagnostic tool. MRI utilizes a combination of a powerful static magnetic field and radio frequency pulses which gather information concerning the location and interrelation of atomic nuclei which possess unpaired electron spin within the body. As hydrogen is the most prevalent element to possess unpaired spin, MRI mainly images hydrogen ion concentration. Based upon this information, a computer is able to generate an anatomic image of the subject. For particular studies, MRI has a distinct advantage over computed tomography (CT) scans. For example, it is presently established that MRI is the diagnostic tool of choice in evaluating the posterior fossa, an anatomical location that is poorly visualized by CT. MRI is also superior to CT in delineating extremity soft-tissue tumors and primary bone malignancies. Whereas CT scans a region of interest in one plane, MRI permits imaging in any desired plane, thus more easily permitting multidimensional mapping of tumors.

These advantages of MRI make it attractive for use in radiation treatment planning. Over the past several years, CT has been used for this purpose and has revolutionized radiation treatment by making available more detailed information concerning tumor localization than was ever before possible: (E. Hart, "The Role of the CT Scanner in RT Planning" 54(613) *Radiotherapy* 20, 1988.) Still, as suggested above, certain anatomical studies are better suited to MRI, and thus, MRI should potentially complement CT in radiation treatment planning. It has also been suggested that MRI may be synergistic with CT in the definition of tumor volume for a number of disease states. (A. Lichter and B. Fraass, "Recent Advances in Radiotherapy Treatment Planning" Oncoloy, May 1988, p. 43)

In order for these expectations to be met, there is a need to develop a means to accurately interface MRI with other diagnostic imaging modalities such as CT or positron emission tomography (PET) and to transfer tumor localization data obtained from MRI and the other imaging modalities to radiation treatment devices. It is important to realize that due to spatial and temporal magnetic field fluctuations within the MRI field, the displayed image is distorted to varying degrees in a non-uniform manner. These fluctuations are dependent on multiple factors such as ambient temperature, and extraneous magnetic fields in the immediate scanner vicinity. Images appearing on the viewing screen (CRT), and ultimately on the film hardcopy, are the result of system software manipulations intended for viewer aesthetics. Further, the bony skeleton which is often used as a reference in determining tumor location and size with other imaging modalities is not well visualized on MRI. Thus, MRI does not permit direct tumor measurement with the degree of consistency and precision demanded in a treatment planning setting.

SUMMARY OF THE INVENTION

The present invention provides an inexpensive but effective means to interface MRI with other diagnostic imaging modalities and radiation treatment devices in a reproducible manner. The invention herein described and claimed avoids the interfacing problems with MRI otherwise caused by distortion and poor visualization of bone by employing a grid system. For MRI, the system uses a grid structure of members of contrast material visualized on MRI and a means for reproducibly positioning said grid structure relative to a body part being imaged. With the grid properly positioned, the image taken with the MRI will include both data relative to the body part and artifact caused by the contrast agent of the grid. As the true spatial relationship of the grid members is known, and the causes of distortion affect the grid and the body part similarly, such grid artifact functions as a reference in the same manner that the bony skeleton serves as a reference with other imaging modalities. Thus, if a tumor is the structure of interest being imaged, determinations of location and size of the tumor are made by reference to the known spatial relationship of the grid.

When the subject is studied using other imaging modalities, the system is again employed changing only the contrast material as required. Using the positioning means, the subject and the grid structure are aligned in the same manner as when the MRI images were made. With the grid as a reference one can readily and accurately compare MRI images with images made with the other imaging modalities. Thus, by selection of contrast material, and a means to precisely and consistently position the grid and the patient in relation one to the other, the invention functions to reproducibly interface MRI with other modalities such as CT, PET and radiation treatment devices. Localization grids have been described for use with CT, PET and MRI applications: (S. Goerss, et al: A Computerized Tomographic Stereotactic Adaptation System, 10 Neurosurgery 375-379, 1982; P.C. Hajek, et. al., Localization Grid for MR-guided Biopsy. 163(3) Radiology 825-826, 1987; S. Miura, et. al. Anatomical Adjustments in Brain Positron Emission Tomography Using CT Images. 12(2) Journal of Computer Assisted Tomography 363-67, 1988; U.S. Pat. No. 4,583,538.) To varying degrees, these grids are either difficult to use, expensive to manufacture, not conducive to exact repositioning from scan to scan or not readily interchangeable between MRI and the various other diagnostic modalities.

Accordingly, it is an object of this invention to provide a method and apparatus which may be used to interface MRI with other imaging devices as well as with radiotherapy treatment units.

Another object of this invention is to provide a method and apparatus to interface MRI with other imaging devices as well as with surgical intervention techniques.

Yet another object of the invention is to satisfy the above stated objectives in an uncomplicated and inexpensive manner.

The novel features which are believed to be characteristic of the invention both as to its organization and method of operation, together with further objectives and advantages thereof, will be better understood from the following drawings in which a presently preferred embodiment of the invention is illustrated by way of example. It is to be expressly understood, however, that the drawings are for the purpose of illustration and description only and are not intended as a definition of the limits of the invention.

DETAILED DESCRIPTION OF THE PREFERRED EMBODIMENT

Figure 1D:
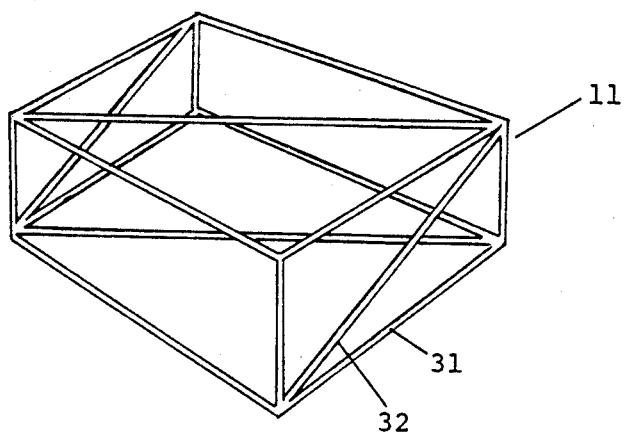
FIGS. 1B through 1D: Perspective views of a variety of grid structures.

While this invention is susceptible of embodiment in many different forms, it is shown in the drawings and will herein be described in detail, preferred embodiments of the invention. It should be understood, however, that the present disclosure is to be considered an exemplification of the principles of the invention and is not intended to limit the invention to the specific embodiments illustrated.

The grid system of the preferred embodiment has two basic components. FIG. 1A illustrates the first component of the system, the grid structure 11. As illustrated, the grid structure of the preferred embodiment is a rectangular structure having two open ends 12. The walls 13 of the grid structure 11 are made of semi-rigid non-magnetic material such as plexiglass. Embedded within the walls are tubes 16, also of a non-magnetic material, containing contrast material. For use with MRI, the preferred contrast material is Gadolinium diethylenetriaminepentaacetic acid (Gd-DPTA). Optimal visualization on both T1- and T2-weighted spin-echo pulse sequences has been obtained by Hajek, et. al., supra, using 5 mm-diameter tubes filled with 500 mM Gd-DPTA. It is to be understood that other paramagnetic material may be substituted for Gd DPTA and still come within the scope of the claims. For use with CT radiopaque contrast material such as Barium is desirable.

The tubes containing contrast material are regularly spaced and arranged in a mutually orthogonal fashion. Also, one of the tubes embedded in each face of the grid structure is arranged so as to form a diagonal 18.

In the presently preferred embodiment, interfacing between diagnostic modalities is accomplished by using identically constructed grid structures having tubes containing contrast material specific for the particular imaging modality being used. Thus, for example, one grid structure having tubes containing Gd-DPTA is used with MRI and an identical structure having tubes containing Barium is used with CT and radiation treatment devices.

Figure 2:
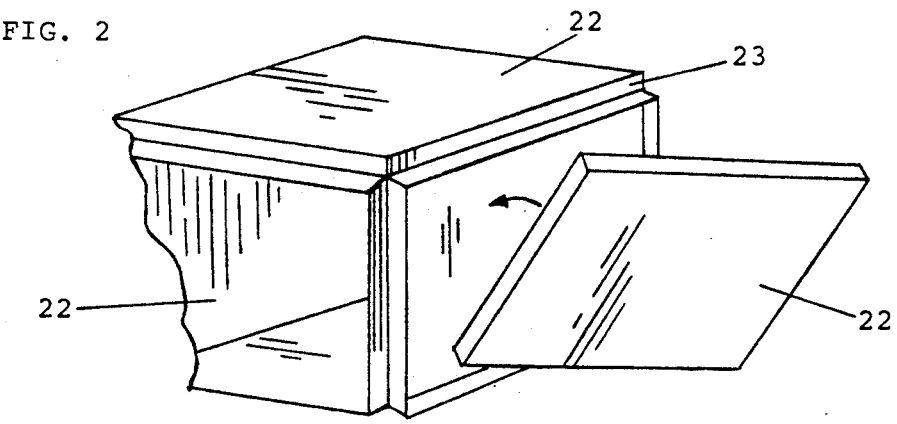
FIG. 2: Partial perspective view of a grid structure having removable walls.

Alternatively, interfacing may be accomplished using a grid structure, as illustrated in FIG. 2, wherein the walls 22 of said structure may be removed and replaced with identically constructed walls with tubes containing a different contrast material. Thus, one would have a set of grid structure walls containing contrast material specific for MRI, a set of walls containing contrast material specific for PET, and yet another set of walls specific for CT and radiation treatment devices. Said grid structure walls would be held in place by conventional framing means manufactured of non-magnetic material 23. An example of suitable material would be semi-rigid nylon or plastic. Alternatively, the walls themselves could have interlocking means at their edges such as a mitered joint type of assembly so as not to require an external frame to hold the walls in place.

Interfacing between MRI, CT and radiotherapy treatment devices is also made possible using a grid structure with tubes containing both paramagnetic and radiopaque contrast material. An example would be a grid structure with tubes containing a solution with sufficient amounts of both Gd-DPTA and Barium sulfate.

Figure 3:
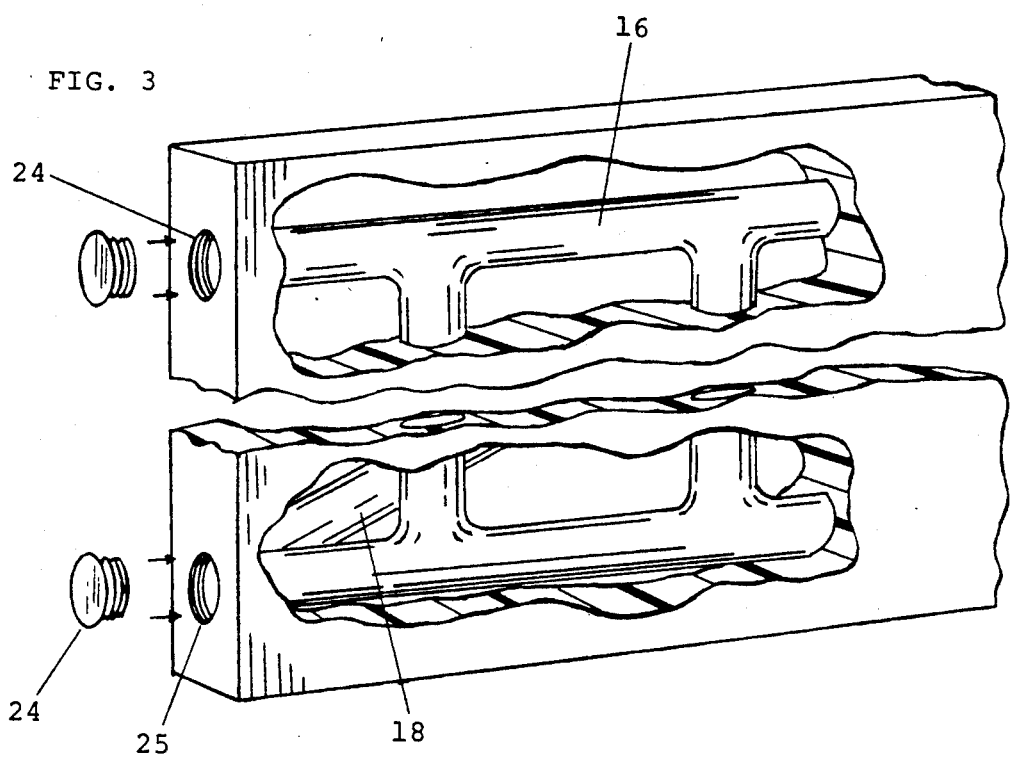
FIG. 3: Perspective view of the corner portions of a grid structure illustrating the interconnected tubing network embedded within said wall, and specifically showing the beginning and terminus portions which open at the same edge and are able to be capped.

An alternative to using separate grid structures or removable grid structure walls is a means to empty and refill the tubing of the wall of contrast material. FIG. 3 illustrates such an embodiment. In this embodiment, the tubes of a wall form an interconnected network, the beginning and terminal portions (26, 25) of which fit flush with the edge of the wall. These end portions open to the outside are fitted with a capping means such as a simple plug or screw cap 24. Thus, to empty the tubing network of contrast material one removes the cap from the beginning and terminus end of the tubing and tips the wall to let the material drain. To refill, one tips the wall up and fills at the beginning until the solution runs out the terminal end. Once refilled, the ends are re-capped.

The ability to empty and refill the tubes of the grid structure is particularly useful when using the grid structure to interface with PET. Imaging with PET is dependent on the emission of positrons. The materials which are generally used as positron emitters have only a short half life and are thus prepared shortly before use.

Figure 4:
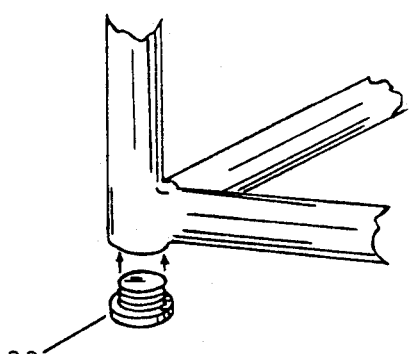
FIG. 4: Partial perspective view of the corner section of the grid structure of FIG. 1D, illustrating the use of a screw plug at such corner section.

FIG. 1D illustrates yet another embodiment of the grid structure of the invention. In this embodiment the grid structure 11 is an assembly of hollow tubes 31 joined in a generally rectangular shape with additional hollow tubes as diagonals 32 across four of the faces of said rectangle. The hollow tubes of this embodiment are formed of a non-magnetic material such as a rigid plastic and filled with a solution of contrast material. As indicated above, the contrast material would be selected with regard to the particular imaging modality being used. Further, as illustrated in FIG. 4, the corners of the grid structure of the embodiment of FIG. 1D contain a screwable plug 33 which allows emptying and refilling the hollow tubes (31, 32) such that solutions containing other preferred types of contrast material are readily substituted as the need arises.

Figure 1C:
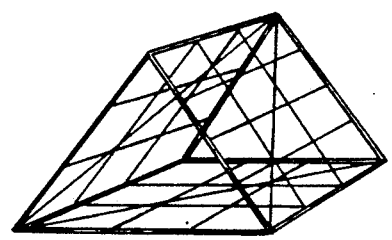
Figure 1B:
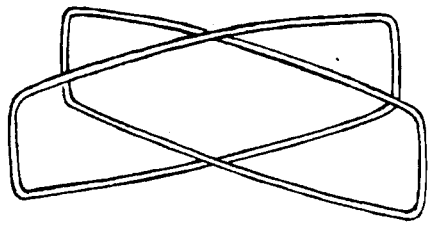
Figure 1A:
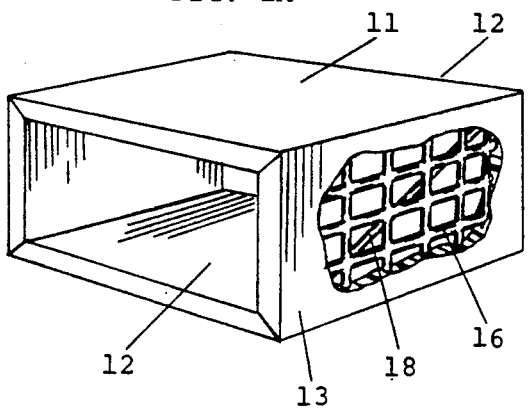
FIG. 1A: Perspective view of a grid structure having a portion of its side wall cut away to expose tubing embedded in the wall.

FIGS. 1B and 1C illustrate other suitable configurations of the grid structure. As will be appreciated, the exact configuration of a grid structure is not important to the essence of the invention. In the same manner, the invention may also be carried out by using contrast material in solid rather than liquid form. For example, contrast material in a defined pattern could be embedded in a matrix of nonmagnetic material or embedded within solid rods or bars that are arranged so as to form a grid.

Figure 5:
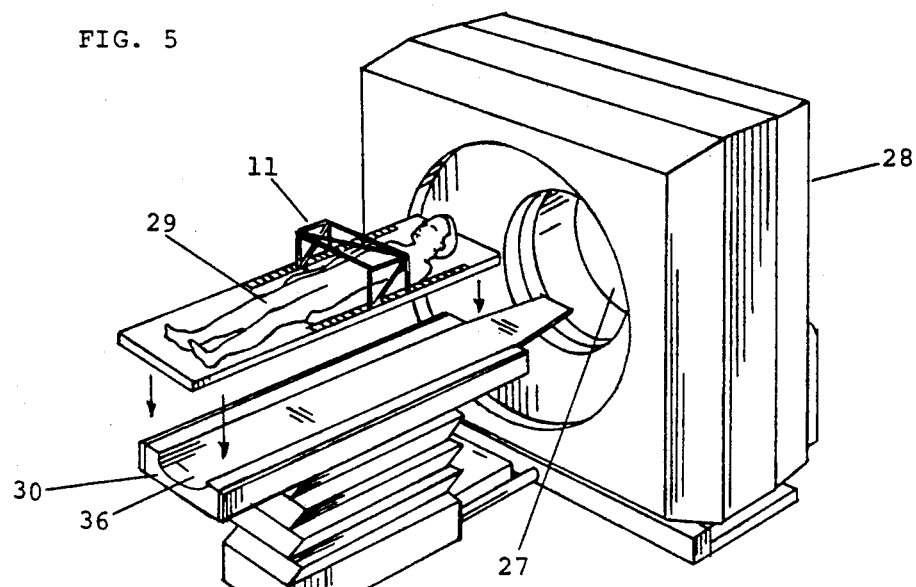
FIG. 5: Perspective view showing the relation of the patient platform to the patient bed of an imaging unit.

Although the exact configuration of the grid structure is unimportant, as illustrated in FIG. 5 the grid structure 11 must be of a size sufficient to fit about the body of the subject 29 being imaged but within the gantry 27 of the diagnostic imaging machine 28 being used.

Figure 6B:
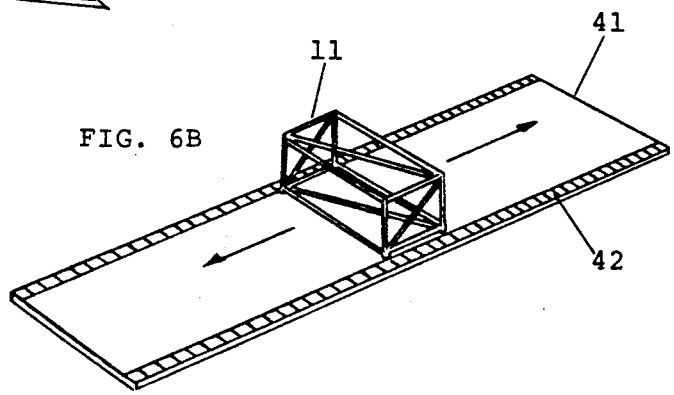
FIGS. 6A and 6B: Two embodiments of a patient platform with grid structure slidably attached.
Figure 6A:
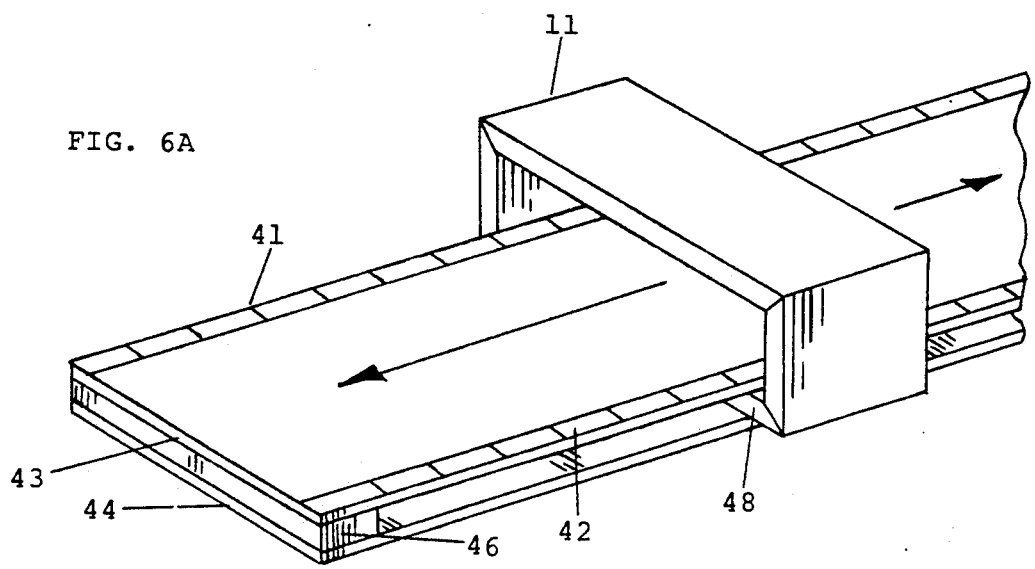

The second component of the grid system is a means for reproducibly positioning the grid system relative to the body part being imaged. In the preferred embodiment, this is accomplished by using a grid locating means and a crossed laser system. As illustrated in FIGS. 6A and 6B, the grid locating means of the preferred embodiment is a patient platform 41 to which the grid 11 is slidably attached such that it may be moved horizontally along the length of said platform and positioned at the appropriate place about the subject being imaged. Located on the top surface of the platform and at either side of the grid is a scale in the form of regularly spaced and numbered demarcations.

Slidable attachment means attaching the grid structure to the platform may be accomplished by a tongue and groove mechanism, a roller and track mechanism or other conventional means.

In the presently preferred embodiment FIG. 6A, the platform consists of an upper member 43 and a lower member 44. The upper member is sufficiently narrow to pass between the side walls of the grid structure, but sufficiently wide so as not to allow lateral movement of the grid structure. As can be seen in FIG. 6A, at each end the members are joined to a spacer 46 such that the upper member is separated from the lower member by a space sufficient to accommodate the bottom wall 48 of the grid structure. The fit of the bottom wall in this space should be such that sliding of the grid back and forth is accomplished without difficulty but it should not be so great as to allow vertical movement of the grid structure. It is desirable to have sufficient horizontal movement of the grid structure such that it can be moved the entire length of an average sized subject centered on the platform. Using the above described construction, the horizontal movement of the grid structure is dictated by the strength and rigidity of the upper member. It is desirable that the upper member support the subject without deformation so that the grid structure is not pinched and prevented from horizontal movement. Thus, the stronger and more rigid the upper member, the greater the span between the supporting spacers 46, and the greater the horizontal movement of the grid structure. As with the grid structure 11, the platform must be manufactured of nonmagnetic material.

FIG. 5 illustrates the relationship of the platform 41 to the patient bed 30 of an imaging unit 28. As illustrated in FIG. 5, the patient platform 41 approximates the dimensions of the patient bed 30 in terms of length and width and rests on top of said patient bed. The patient bed for the conventional MRI unit as well as for the conventional CT unit has a generally convex surface 36. The provision of a patient platform as illustrated in FIG. 5 transforms the generally convex surface of the patient bed to a flat surface. Means may be provided to conform the bottom surface of the patient platform 41 to the concavity 36 of the patient bed so as to prevent said patient platform from moving about while it rests on the surface of the patient bed. Commercial patient platforms are available from such manufacturers as Pickering and General Electric Medical Systems. Said commercial patient platforms can be adapted to receive the grid structure as illustrated in FIG. 5 and would fall within the scope of the claims of this invention.

Figure 7A:
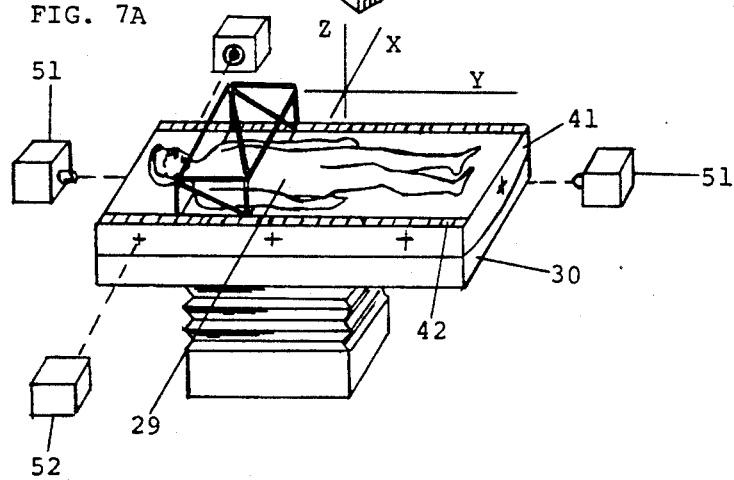
FIGS. 7A and 7B: Perspective view illustrating the use of saggital and transverse lasers to align the patient platform and subject.
Figure 7B:
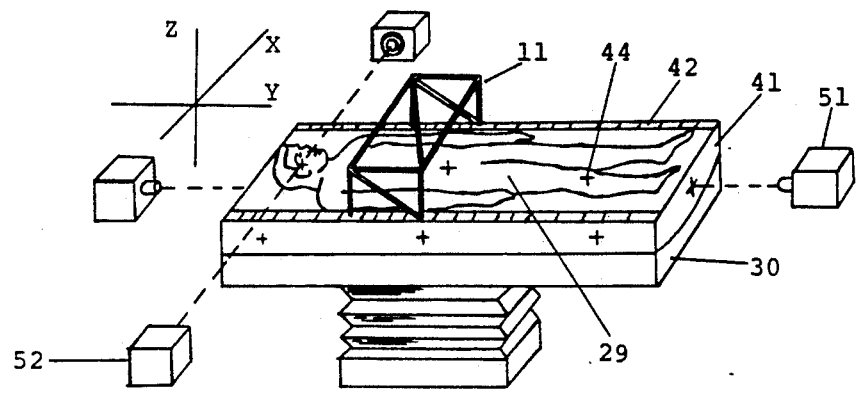

FIGS. 7A and 7B illustrate the crossed laser system which, together with the grid locating means, is used to reproducibly position the subject in relation to the grid. As illustrated in FIGS. 7A and 7B, the saggital laser 51 aligns the platform and subject in the X and Z coordinates whereas the transverse laser 52 aligns the subject and platform in the Y and Z coordinates. Crossed laser systems are available commercially and can be readily adapted to the use described herein. An example of a commercially available system is the *Patient Positioning Systems* from Gammex Inc., P.O. Box 26708 Milwaukee, Wis. 53226.

METHOD OF USE

In FIG. 7A, the patient platform 41 with grid structure 11 is mounted on the patient bed of the imaging unit 28. The patient platform is then aligned via the crossed laser system utilizing sagittal 51 and transverse 52 lasers. The use of a crossed laser technique to align structures in three dimensional space is known in the art. In relation to the present invention, the sagittal and transverse lasers are fixed and define a point in X, Y and Z coordinates to which the patient platform is related. The sagittal laser defines the X and Z coordinates of the patient platform 41 in relation to the imaging unit table 30, while the transverse laser allows for adjustments in the Y and Z coordinates. By recording the X, Y and Z coordinates of the imaging unit table with respect to some initial point of laser intersection on the table, the location of the patient platform 41 is reproducible from room to room, or from imaging device to imaging device.

With the subject 29 for imaging stationed on the patient platform 41, standard body immobilization techniques such as body casting or pleximolds can be employed. As illustrated in FIG. 7B, the sagittal and transverse lasers are then used to position the subject with relation to the table and the desired X, Y and Z coordinates. Positioning of the subject 29 is accomplished by employing marks or ink tattoos 44 on either the subject or immobilization devices.

Figure 8A:
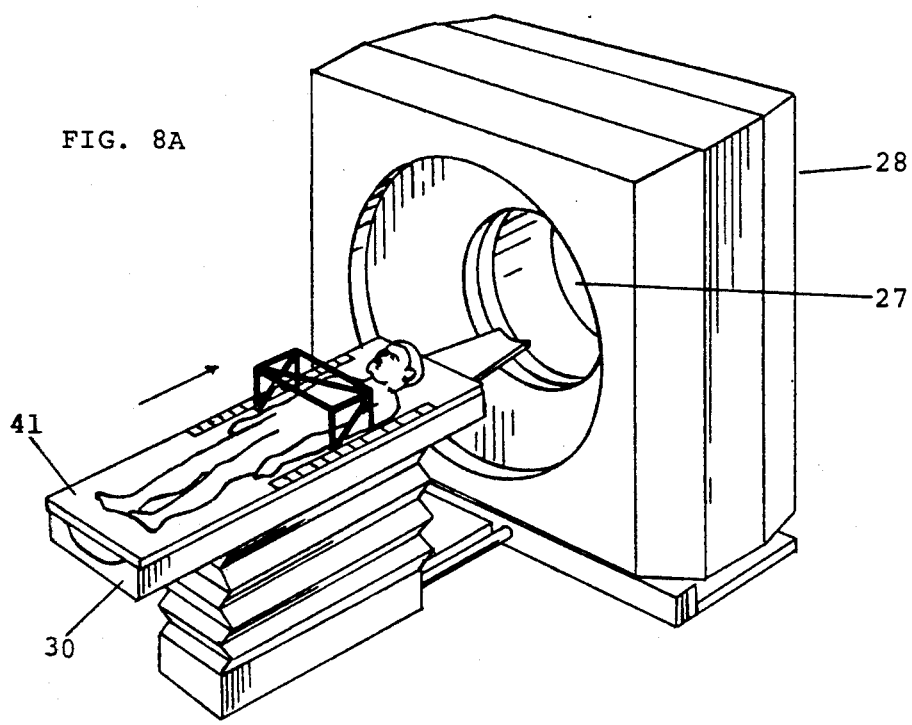
FIG. 8A: Perspective view of the subject on the patient platform with grid structure slidably attached in preparation for moving into the gantry of an imaging unit.
Figure 8B:
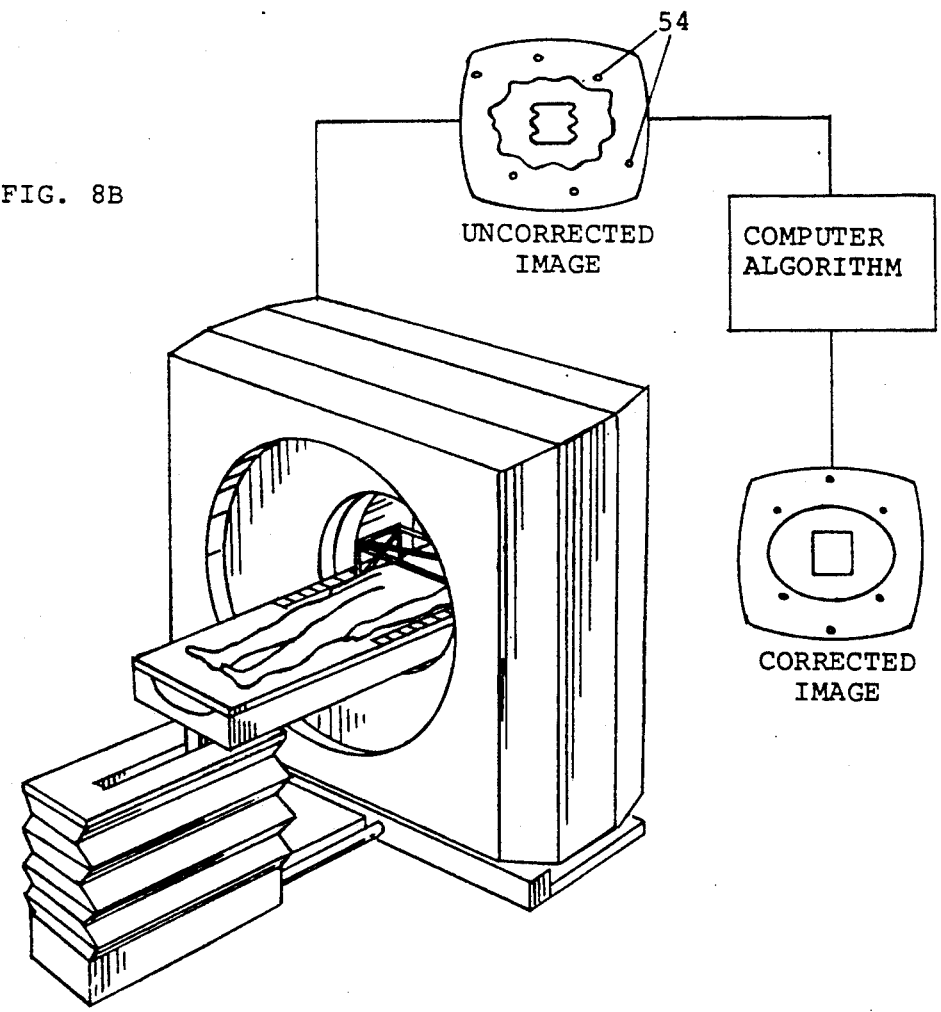
FIG. 8B: Perspective view of the subject on the patient platform with grid attached positioned within the gantry of an imaging unit and diagrammatic representation of the use of a computer algorithm to correct image distortion.

The grid structure 11 is then positioned so as to flank the region of interest of the subject 29 which is to be imaged. In the preferred embodiment, the location of the grid structure, once positioned, is indicated by the numbered demarcations 42 provided on each side of the platform. These numbered demarcations are recorded, and the table with the grid structure platform and subject is then passed into the gantry 27 of the imaging device 28 and the region of interest is scanned as illustrated in FIGS. 8A and 8B.

When the subject is studied with imaging modalities other than MRI the appropriate contrast material is selected and the above described procedure is repeated. For example, if the subject is also to be studied using CT, a grid structure and patient platform identical but for the contrast material contained within the tubes is mounted on the CT patient bed. In the case of CT, barium or other radiopaque contrast material is used. The platform is aligned using the cross laser system as described above; the subject is stationed on the platform; the subject is laser aligned and the grid structure is then positioned over the region of interest using the numbered demarcations.

Using the above method, the region of interest as studied with MRI is defined in terms of the grid. As the grid pattern and the position of the subject relative to the grid is identical in the CT studies as with the MRI studies direct comparison between the studies of the two different modalities can be made in spite of the distortion obtained with MRI.

As should be appreciated, the above-described grid system and procedure can be used to interface MRI with any other imaging modality including PET and Digital Subtraction Angiography.

The grid system and procedure also provides a means to more accurately follow the course of a disease state and to judge the effectiveness of a treatment plan on that disease state. For example, if one is treating a tumor with radiotherapy, it is desirable to periodically repeat MRI and CT scans of the tumor in order to monitor the treatment. Because of the distortion obtained with MRI, it is difficult to assess minute changes in tumor location and size. Using the grid system and procedure described above, one avoids the inherent distortion obtained with MRI. Because the system and procedure permit exact repositioning of the subject relative to the grid structure during repeated scans and because the tumor is defined in terms of the grid, small changes in tumor size or location can be monitored.

For radiotherapy purposes, using the methods and apparatus of the present invention, a tumor defined by MRI (including coronal and sagittal sections) may thus be more accurately translated to CT images (which are by necessity transverse), with a resultant improvement in target volume determination. In the case of computer enhanced dosimetry, CT imaging cannot be bypassed as it provides important electron density information. In the case of coplaner radiation, a tumor may be defined in X, Y and Z coordinates, and a simpler connect-the-dot method of target volume determination is employed. The accuracy of this can be easily checked at a therapy simulator or treatment machine using an array of lead wires instead of the gadolinium chloride or barium sulfate which are well visualized via MRI and CT respectively. The invention is also adaptable to MRI-guided needle biopsy, or PET-guided biopsy.

METHOD OF USING THE GRID SYSTEM TO CORRECT MRI DISTORTION

Although the invention herein described can be used inspite of the distortion caused by magnetic field fluctuations in MRI, it may also be used as a means to correct such distortion. As before mentioned, the magnetic field fluctuations distort the image of the grid artifact in the same manner as such magnetic field fluctuations distort the image of the subject. The grid artifacts which can be directly related to the known spatial relationship of the grid thus act as indices of the degree of distortion present in a particular image. By manipulating the image so as to bring the grid artifacts into proper relation to one another, the image distortion of the subject would be simultaneously corrected. Such manipulation can be done using conventional mathematical computations which are known in the art.

As illustrated in FIG. 8B, the above described method can be accomplished by using a computer algorithm which applies the required mathematical procedures to remove image distortion. In this manner, the computer algorithm means can be incorporated with the software of the MRI to recognize the misalignment of grid artifact 54, manipulate the uncorrected image to bring the grid artifact into proper alignment and thus produce a corrected image.

What I claim is:

1. A method for interfacing an image of a body part of a patient made with an MRI system with an image of the same body part made with a non-MRI imaging system, the MRI and non-MRI imaging system having a gantry into which the patient reclining on a longitudinal patient bed is introduced, the method for interfacing comprising the steps of:
    (a) forming a grid of regularly spaced members containing a contrast material with respect to each type of imaging system, said grid having sufficient size and shape so as to at least partially encompass the patient;
    (b) slidably attaching said grid to a patient platform on which the patient reclines, said platform adapted to fit on top of the patient bed and said platform having means for horizontal movement of said grid along the length of said platform and means for determining the location of said grid along the length of said platform;
    (c) reproducibly locating said grid adjacent the body part to be imaged;
    (d) using a crossed laser system to reproducibly position the patient and said grid within the gantry of said MRI system;
    (e) imaging the body part with said MRI system such that data relative to both the patient and said grid is acquired;
    (f) repeating steps (c) and (d) with said non-MRI system;
    (g) imaging the same body part with said non-MRI system such that data relative to both the patient and said grid is acquired; and
    (h) using the data relative to said grid as a reference to correlate the data acquired with the MRI system and the non-MRI system.

2. A grid and patient alignment system for acquiring data in the course of producing an image of a body part of a patient, with an MRI system and at least one other non-MRI imaging system the MRI system and non-MRI system having a gantry into which the patient reclining on a longitudinal patient bed is introduced, the grid and alignment system comprising:
    (a) grid means for including a contrast material with respect to each type of imaging system, said grid means having sufficient size and shape so as to at least partially encompass the patient;
    (b) a patient platform adapted to fit on a patient bed;

(c) means for slidably attaching said grid means to said patient platform such that said grid means can be moved horizontally along the length of said patient platform;

(d) means for determining the location of said grid means along the length of said patient platform whereby said grid means can be reproducibly located adjacent the body part being imaged; and (e) crossed laser means for reproducibly positioning the patient and said grid means for use within a gantry of the MRI or non-MRI imaging system such that data relative to both the patient and said grid is acquired whereby the data relative to said grid is used as a reference for correlating the data acquired with the MRI and non-MRI system.

3. A method for interfacing an image of a body part of a patient made with an MRI system with an image of the same body part of the patient made with a non-MRI imaging system comprising the steps of:

(a) forming a grid of contrast material;

(b) reproducibly locating said grid adjacent the body part;

(c) reproducibly positioning the patient and said grid in three dimensional space;

(d) maintaining said grid in the location of step (b), and the patient and said grid in the position of step (c), while making an image with the MRI system of the body part and said grid such that the image contains data relative to both the body part and said grid;

(e) locating said grid in the same location as in step (b) and positioning the patient and grid in the same relative position in step (c), and while maintaining the same location and position making an image of the same body part with the non-MRI system; and (f) using the data relative to said grid as a reference to correlate the data acquired with the MRI system and the non-MRI system.

4. In an MRI system and at least one non-MRI imaging system of the type which includes means for imaging an opaque body part, the improvement comprising:

(a) a grid including regularly spaced members containing contrast material with respect to each type of imaging system, said grid having sufficient size and shape so as to at least partially encompass a patient; said grid located proximate the body part to be imaged such that data relative to both patient and said grid is acquired on an image with each type of imaging system; said grid slidably attached to a patient platform on which the patient reclines;

(b) said platform configured to fit on top of a patient bed and having means for horizontally moving said grid along said platform and means for determining the location of said grid along the length of said platform;

(c) a crossed laser system to reproducibly position the patient and said grid within a gantry of each type of imaging system; and (d) a data cooperator for using data relative to said grid as a reference to correlate data acquired with the MRI system and the non-MRI system.

* * * * *